United States Patent [19]

Hartman et al.

[11] Patent Number: 4,929,549

[45] Date of Patent: May 29, 1990

[54] 5-CARBAMOYLTHIENO[2,3-B]THIOPHENE-2-SULFON-AMIDES AS TOPICALLY ACTIVE CARBONIC ANHYDRASE INHIBITORS

[75] Inventors: George D. Hartman, Lansdale; John D. Prugh, Chalfond, both of Pa.

[73] Assignee: Merck & Co., Inc., Rahway, N.J.

[21] Appl. No.: 307,800

[22] Filed: Feb. 8, 1989

[51] Int. Cl.$^5$ .................. C07D 295/12; C07D 265/30; C07D 495/02

[52] U.S. Cl. .............................. 514/227.8; 514/231.5; 514/443; 544/59; 549/50

[58] Field of Search ................... 514/443, 227.5, 231.5; 549/50; 544/59, 178; 435/184

[56] References Cited

U.S. PATENT DOCUMENTS

| | | | |
|---|---|---|---|
| 3,733,322 | 5/1973 | Wright, Jr. .......................... | 549/50 |
| 4,386,098 | 5/1983 | Woltersdorf et al. ............... | 514/367 |
| 4,416,890 | 11/1983 | Woltersdorf et al. ............... | 514/333 |
| 4,426,388 | 1/1984 | Woltersdorf et al. ............... | 514/367 |
| 4,668,697 | 5/1987 | Shepard et al. ..................... | 514/443 |
| 4,677,115 | 6/1987 | Baldwin et al. ..................... | 514/432 |
| 4,798,831 | 1/1989 | Prugh et al. ........................ | 514/253 |
| 4,806,562 | 2/1989 | Hartman et al. .................... | 514/443 |

FOREIGN PATENT DOCUMENTS 0146263 6/1985 European Pat. Off. ............. 549/50

OTHER PUBLICATIONS

Hartough, Chemistry of Heterocycles, Thiophene Interscience Publishers, New York, 1952, pp. 418–419.

*Primary Examiner*—Anton H. Sutto
*Assistant Examiner*—E. C. Ward
*Attorney, Agent, or Firm*—Edward W. Murray; Michael C. Sudol

[57] ABSTRACT

Novel 5-carbamoylthieno[2,3-b]thiophene-2-sulfonamides and derivatives thereof are prepared in reactions of 5-methoxycarbonylthieno-[2,3-b]thiophene-2-sulfonamide with alkylamines, alkoxyalkylamines and hydroxyalkylamines. These compounds are useful for the treatment of elevated intraocular pressure in compositions including ophthalmic drops and inserts.

6 Claims, No Drawings

5-CARBAMOYLTHIENO[2,3-B]THIOPHENE-2-SULFON-AMIDES AS TOPICALLY ACTIVE CARBONIC ANHYDRASE INHIBITORS

SUMMARY OF THE INVENTION

This invention relates to novel 5-carbamoyl-thieno[2,3-b]thiophene-2-sulfonamides which are useful in the reduction of elevated intraocular pressure. More particularly this invention relates to compounds having the structural formula:

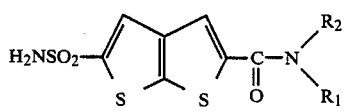

wherein $R_1$ and $R_2$ are hereinafter defined, as well as the pharmaceutically and ophthalmologically acceptable salts thereof. This invention also relates to pharmaceutical compositions for systemic and ophthalmic use employing a novel compound of this invention as active ingredient for the treatment of elevated intraocular pressure, especially when accompanied by pathological damage such as in the disease known as glaucoma. This invention also relates to processes for the preparation of 5-carbamoylthieno[2,3-b]thiophene-2-sulfonamides.

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advanes were made in the treatment of glaucoma since pilocarpine and physostigmine were introduced. Only recently have clinicians noted that many β-adrenergic blocking agents are effective in reducing intraocular pressure. While many of these agents are effective in reducing intraocular pressure, they also have other characteristics, e.g. membrane stabilizing activity, that are not acceptable for chronic ocular use. (S)-1-tert-Butylamino-3[(4-morpholino-1,2,5-thiadiazol-3yl)oxy]-2-propanol, a β-adrenergic blocking agent, was found to reduce intraocular pressure and to be devoid of many unwanted side effects associated with pilocarpine and, in addition, to possess advantages over many other β-adrenergic blocking agents, e.g. to be devoid of local anesthetic properties, to have a long duration of activity, and to display minimal tolerance.

Although pilocarpine, physostigmine and the β-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors, block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available for clinical use.

However, topically effective carbonic anhydrase inhibitors are reported in U.S. Pat. Nos. 4,386,098; 4,416,890; 4,426,388; and 4,668,697, where the compounds reported therein are 5 (and 6)-hydroxy-2-benzothiazole-sulfonamides and acyl esters thereof and 5-(and 6)-hydroxy-2-sulfamoylbenzothiophenes and esters thereof, U.S. Pat. No. 4,677,115, where the compounds are reported to be 5,6-dihydro-thienothiophene sulfonamides, U.S. Pat. No. 4,798,831 where the compounds are reported to be thienofuran sulfonamides and U.S. Pat. No. 4,806,562 where the compounds are reported to be alkylenethienothiophene sulfonamides.

DETAILED DESCRIPTION OF THE INVENTION

The novel compounds of this invention have structural formula:

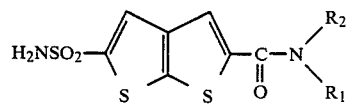

or an ophthalmologically or pharmaceutically acceptable salt thereof, wherein $R_1$ and $R_2$ are independently selected from hydrogen or $C_{1-6}$ straight or branched alkyl, either unsubstituted or substituted with one or more groups chosen from:
amino;
($C_{1-6}$ alkyl)amino;
di($C_{1-3}$ alkyl)amino;
di[($C_{1-3}$ alkoxy)-$C_{2-4}$ alkyl]amino;
di[($C_{1-3}$ alkoxy)-$C_{2-4}$ alkyl]amino;
[$C_{1-3}$ alkoxy-($C_{2-4}$ alkoxy)$_n$]($C_{2-6}$ alkyl)amino, wherein n=1–4;
di[$C_{1-3}$ alkoxy-($C_{2-4}$ alkoxy)$_n$]($C_{2-6}$ alkyl)-amino, wherein n=1–4;
[$C_{1-3}$ alkoxy-($C_{2-4}$ alkoxy)$_n$][$C_{1-3}$-alkoxy)$_m$]($C_{1-6}$ alkyl)amino, wherein n and m=1–4;
$C_{1-4}$ alkoxy;
$C_{1-4}$ alkoxy-($C_{2-4}$ alkoxy)$_n$, wherein n=1–4;
$C_{1-6}$ alkylamino-($C_{2-4}$ alkoxy)$_n$, wherein n=1–4;
di($C_{1-6}$ alkyl)amino-$C_{2-4}$ alkoxy)$_n$ wherein n=1–4;
amino-($C_{2-4}$ alkoxy)$_n$ wherein n=1–4; hydroxy;
$C_{1-3}$ alkylthio;
$C_{1-3}$ alkylsulfonyl;
$C_{1-3}$ alkylsulfinyl;
morpholino;
thiomorpholino;
thiomorpholino-S-oxide;
thiomorpholino-S-dioxide;

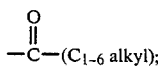

-continued

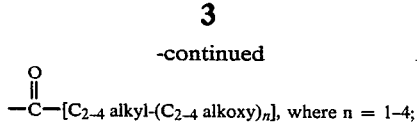
where n = 1-4;

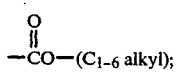

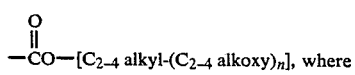
where n = 1-4;

provided that no more than one heteroatom is bonded to any one carbon.

Preferred species of the invention are:
5-[N-(2,2-Dimethylaminoethyl)carbamoyl]thieno[2,3-b]-thiophene-2-sulfonamide;
5-(N-Methylcarbamoyl)thieno[2,3-b]thiophene-2-sulfonamide;
5-(N-Methoxyethoxypropylcarbamoyl)thieno[2,3-b]-thiophene-2-sulfonamide;
5-[N-(3-Oxo-3-thia-n-butyl)carbamoyl]thieno[2,3-b]-thiophene-2-sulfonamide;
5-[N-(2,3-Dihydroxypropyl)carbamoyl]thieno[2,3-b]-thiophene-2-sulfonamide;
5-[N,N-Bis(Hydroxyethyl)carbamoyl]thieno[2,3-b]-thiophene-2-sulfonamide;
5-[N-2-(N'-Morpholino)ethylcarbamoyl]thieno[2,3-b]-thiophene-2-sulfonamide;
5-[N-2-(N'-Thiomorpholino)ethylcarbamoyl]-thieno[2,3-b]thiophene-2-sulfonamide;
5-{N-[N',N'-Bis(2-Methoxyethyl)aminoethyl]carbamoyl}-thieno[2,3-b]thiophene-2-sulfonamide;
and pharmaceutically acceptable salts thereof.

The processes for preparing the novel compounds of the invention are shown by the following schematic illustration:

the excess solvent (and ammonia, if any) may be evaporated in vacuo.

The preferred process for preparing compounds of this invention wherein $R_1$ and/or $R_2$ is alkoxyalkyl comprises refluxing 5-methoxycarbonylthieno[2,3-b]thiophene-2-sulfonamide and an alkoxyalkylamine in alcohol for 1 to 240 hours, preferably in the range of 90 to 100 hours. After cooling, the excess solvent may be evaporaed in vacuo.

Crystallization may be achieved by any of a number of suitable methods. In the preparation of 5-(methylamino)carbonylthieno[2,3-b]thiophene-2-sulfonamide, trituration of the reaction product with methanol and drying has been found to be effective. In the preparation of 5-(N-methoxyethoxypropylcarbamoyl)-thieno[2,3-b]thiophene-2-sulfonamide, addition of ether to the resulting product and recrystallization of the final compound from 1,2-dichloroethane has been found effective.

The hydrochloride salts of this invention are prepared by reacting a 5-carbamoylthieno-[2,3-b]thiophene-2-sulfonamide having a basic substituent dissolved in alcohol with a solution of hydrochloric acid in alcohol. Crystallization may be achieved by any suitable method. In the preparation of 5-[N-(2,2-dimethylaminoethyl)]carbamoylthieno[2,3-b]thiophene-2-sulfonamide hydrochloride, crystallization has been successfully achieved by scratching and cooling the solution for several hours.

For use in treatment of conditions relieved by the inhibition of carbonic anhydrase, the active compound can be administered either systemically, or, in the treatment of the eye, topically. The dose administered can be from as little as 0.1 to 25 mg or more per day, singly, or preferably on a 2 to 4 dose per day regimen although a single dose per day is satisfactory.

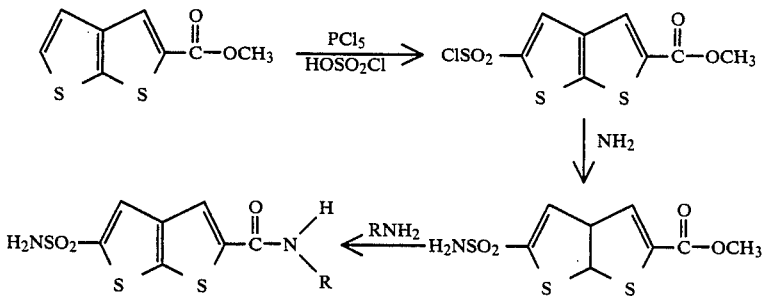

5-Methoxycarbonylthieno[2,3-b]thiophene-2-sulfonamide, a key intermediate for many of the novel compounds of this invention, is obtained by adding methylthieno[2,3-b]thiophene-2-carboxylate to a mixture of phosphorus pentachloride and chlorosulfonic acid to yield 5-methoxycarbonylthieno[2,3-b]thiophene-5-sulfonylchloride. This latter compound is then dissolved in an inert organic solvent and added dropwise to an excess of ammonium hydroxide with stirring. 5-Methoxycarbonylthieno[2,3-b]thiophene-2-sulfonamide is obtained by evaporating the excess ammonia and solvent.

The preferred process for preparing compounds of this invention wherein $R_1$ and/or $R_2$ is alkyl comprises heating 5-methoxycarbonylthieno[2,3-b]thiophene-2-sulfonamide suspended in alcohol or equivalent solvent in the presence of an alkylamine under pressure for 1 to 72 hours, preferably about 20 hours, until the reaction is substantially completed. The mixture is then cooled and When adminstered for the treatment of elevated intraocular pressure or glaucoma, the active compound is most desirably administered topically to the eye, although systemic treatment is, as indicated, also possible.

When given systemically, the drug can be given by any route, although the oral route is preferred. In oral administration, the drug can be employed in any of the usual dosage forms such as tablets or capsules, either in a contemporaneous delivery or sustained release form. Any number of the usual excipients or tableting aids can likewise be included.

When given by the topical route, the active drug or an ophthalmologically acceptable salt thereof such as the hydrochloride salt is formulated into an opthalmic preparation. In such formulations, from 0.1% to 15% by weight can be employed. The objective is to administer a dose of from 0.1 to 1.0 mg per eye per day to the patient, with treatment continuing so long as the condition persists.

Thus, in an ophthalmic solution, insert, ointment or suspension for topical delivery, or a tablet, intramuscular, or intravenous composition for systemic delivery, the active medicament or an equivalent amount of a salt thereof is employed, the remainder being carrier, excipients, preservatives and the like as are customarily used in such compositions.

The active drugs of this invention are most suitably administered in the form of ophthalmic pharmaceutical compositions adapted for topical administration to the eye such as a suspension, ointment, or as a solid insert. Formulations of these compounds may contain from 0.01 to 15% and especially 0.5% to 2% of medicament. Higher dosages as, for example, about 10%, or lower dosages can be employed provided the dose is effective in reducing or controlling elevated intraocular pressure. As a unit dosage from between 0.001 to 10.0 mg, preferably 0.005 to 2.0 mg, and especially 0.1 to 1.0 mg of the compound is generally applied to the human eye, generally on a daily basis in single or divided doses so long as the condition being treated exists.

These hereinbefore described dosage values are believed accurate for human patients and are based on the known and presently understood pharmacology of the compounds, and the action of other similar entities in the human eye. They reflect the best mode known. As with all medications, dosage requirements are variable and must be individualized on the basis of the disease and the response of the patient.

The pharmaceutical preparation which contains the active compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or arylalkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The pharmaceutical preparation may also be in the form of a solid insert such as one which after dispensing the drug remains essentially intact, or a bio-erodible insert that is soluble in lacrimal fluids, or otherwise disintegrates.

EXAMPLE 1

5-[N-(2,2-Dimethylaminoethyl)carbamoyl]thieno-[2,3-b]thiophene-2-sulfonamide

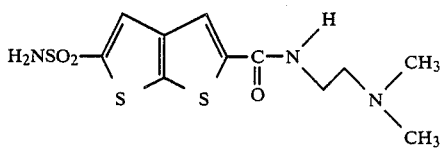

Step A: Preparation of 5-Methoxycarbonylthieno-[2,3-b]thiophene-2-sulfonylchloride Crystals of phosphorus pentachloride (9.80 g., 47.1 mmoles) were added in portions to chlorosulfonic acid (9 ml., 15.4 g., 132 mmoles) in an inert atmosphere. The solution was stirred for 15 minutes. To this solution small portions of methyl thieno[2,3-b]thiophene-2-carboxylate (8.49 g., 42.8 mmoles) were slowly added, allowing for subsiding of effervescence between additions. After the addition was complete, the solution was stirred in an inert atmosphere for 25 minutes. The resulting solution was poured carefully onto ice-water. The resulting mixture was triturated and the off-white crystals were collected and washed with water and dried in vacuo over phosphorus pentoxide to give 11.58 g of 5-methoxycarbonylthieno[2,3-b]thiophene-2-sulfonylchloride. This was used in the next step without purification.

Step B: Preparation of 5-Methoxycarbonylthieno[2,3-b]thiophene-2-sulfonamide To stirred ammonium hydroxide (150 ml) was added dropwise 5-methoxycarbonylthieno[2,3-b]thiophene-2-sulfonyl chloride (11.58 g. 39.02 mmoles) dissolved in acetone (140 ml). After the addition was complete, the solution was stirred for 30 minutes. The reaction was worked up by evaporating the ammonia and acetone in vacuo. The crystals were collected and dried (9.66 g.) (89%). Recrystallization from nitromethane gave 7.02 g. mp 219°–220° C.

Calc. for $C_8H_7NO_4S_3$: C, 34.65; H, 2.54; N, 5.05. Found: C, 35.00; H, 2.51; N, 5.20.

Step C: Preparation of 5-[N-(2,2-Dimethylaminoethyl)-carbamoyl]thieno[2,3-b]thiophene-2-sulfonamide 5-Methoxycarbonylthieno[2,3-b]thiophene-2-sulfonamide (0.55 g., 2 mmoles) was suspended in methanol (5 ml). N,N-dimethylaminoethylamine (0.53 g., 2 mmoles) was added and the mixture refluxed for 3 days. The mixture was cooled in an ice-water bath and the product collected and washed with cold methanol. The dried product weighed 0.45 g. which was used directly to make the HCl salt.

Step D: Preparation of 5-[N-(2,2-Dimethylaminoethyl)carbamoyl]thieno[2,3-b]thiophene-2-sulfonamide hydrochloride 5-[N-(2,2-Dimethylaminoethyl)carbamoyl]-thieno[2,3-b]thiophene-2-sulfonamide (0.45 g., 1.35 mmole) was dissolved in hot ethanol (100 ml) filtered and cooled. To this solution was added 0.265 ml of

7

5.10M HCl in methaol. The resulting solution was stirred and scratched then cooled in a refrigerator overnight. The resulting crystalline product, 0.46 g., mp 254°–255° C. (D), was collected and dried.

EXAMPLE II
5-(N-Methylcarbamoyl)thieno[2,3-b]thiophene-2-sulfonamide

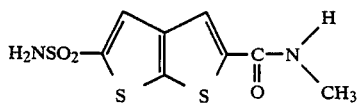

5-Methoxycarbonylthieno[2,3-b]thiophene-2-sulfonamide (1.11 g., 4 mmol) and 3.60M. methylamine in methanol (20 mL., 2 mmole) were heated in a pressure bomb at 60° C. bath temperature for 20 hours. The mixture was cooled to room temperature and the excess methylamine and methanol were evaporated in vacuo. The resulting solid was triturated with methanol and dried to give 1.06 g. of 5-(N-methylcarbamoyl)thieno[2,3-b]thiophene-2-sulfonamide. m.p. 272°–273° C.

Calc. for $C_8H_8N_2O_3S$: C, 34.77; H, 2.92; N, 10.14. Found: C, 34.77; H, 2.88; N, 10.11.

EXAMPLE III
5-(N-Methoxyethoxypropylcarbamoyl)thieno[2,3-b]thiophene-2-sulfonamide

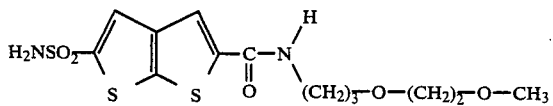

5-Methoxycarbonylthieno[2,3-b]thiophene-2-sulfonamide (0.55 g., 2 mmoles) and 3-(methoxyethoxy)propylamine (0.80 g., 6 mmoles) were refluxed in methanol (5 mL) for 96 hours. The solution was cooled and evaporated in vacuo to remove most of the methanol. Ether was added and the resulting product was recrystallized from 1,2-dichloroethane to give 0.49 g of 5-(N-methoxyethoxypropylcarbamoyl)thieno[2,3-b]thiophene-2-sulfonamide, m.p. 154°–155° C.

Calc. for $C_{13}H_{17}N_2O_5S_3$: C, 41.36; H, 4.54; N, 7.42. Found: C, 41.40; H, 4.75; N, 7.40.

EXAMPLE IV
5-[N,N-Bis(Hydroxyethylcarbamoyl)]thieno[2,3-b]thiophene-2-sulfonamide

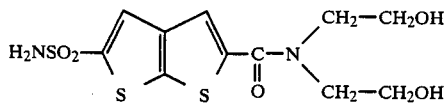

5-Methoxycarbonylthieno[2,3-b]thiophene-2-sulfonamide (1.11 g., 4 mmoles); bis(hydroxyethyl)amine (2.10 g., 20 mmoles); and anhydrous bis(methoxyethyl)ether (5 mL) were heated at bath temperatures of 110° to 120° C. for 6 hours. The reaction was cooled to room temperature and poured into water (20 mL). Concentrated hydrochloric acid was added until strongly acidic. The mixture was extracted with ethyl acetate five times. The combined ethyl acetate extracts were washed with water, dried (MgSO4) filtered and the solvent removed in vacuo to leave a solid which was washed by decantation three times with ether. This crude material was chromatographed on a 50×150 mm column of silica gel eluting with 10% methanol in chloroform, to give 0.44 g of product, which was further purified by HPLC (waters C-18; 30×6.39; buffer 1 mL H3PO4/liter of water) reverse phase to give 0.16 g of pure 5-[N,N-Bis(hydroxyethylcarbamoyl)]thieno[2,3-b]thiophene-2-sulfonamide, m.p. 155°–156° C.

Calc. for $C_{11}H_{14}N_2O_5S_3$: C, 37.70; H, 4.03; N, 7.99. Found: C, 37.31; H, 3.81; N, 7.84.

EXAMPLE V
5-(N-2,3-Dihydroxypropylcarbamoyl)thieno[2,3-b]thiophene-2-sulfonamide

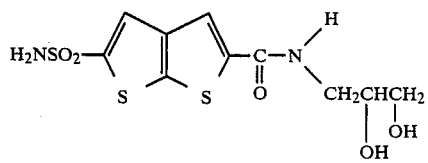

5-Methoxycarbonylthieno[2,3-b]thiophene-2-sulfonamide (0.83 g., 3 mmoles) and 2,3-dihydroxypropylamine (1.37 g., 15 mmoles) were dissolved in hot methanol and refluxed for 48 hours. The reaction was worked up by evaporating the methanol in vacuo. Water (7 mL) was added followed by the dropwise addition of conc. HCl until strongly acidic (~1.8 pH). The product crystallized out and was collected, washed with water and dried to give 0.90 g of crude product. Recrystallization from nitromethane gave 0.73 g of 5-(N-2,3-dihydroxypropylcarbamoyl)thieno[2,3-b]thiophene-2-sulfonamide, m.p. 117°–118° C.

EXAMPLE VI
5-[N-(3-Oxo-3-thia-n-butyl)carbamoyl]thieno[2,3-b]thiophene-2-sulfonamide

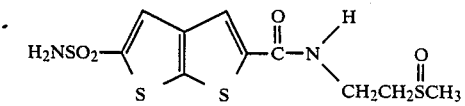

Step A:
5-[N-(3-Thia-n-butyl)carbamoyl]thieno[2,3-b]thiophene-2-sulfonamide

5-Methoxycarbonylthieno[2,3-b]thiophene-2-sulfonamide (1.11 g., 4 mmoles), 2-thia-n-butylamine (2.92 g., 32 mmoles) and methanol were refluxed with stirring for 5 days. The solution was cooled in the freezer for 2 hours and the product was filtered off to yield 1.10 g of 5-[N-(3-thia-n-butyl)carbamoyl]thieno[2,3-b]thiophene-2-sulfonamide which was used in the next step without further purification.

Step B:
5-[N-(3-Oxo-3-thia-n-butyl)carbamoyl]thieno[2,3-b]thiophene-2-sulfonamide Sodium periodate (1.40 g., 6.54 mmoles) was dissolved in water (20 mL). THF (20 mL) was added followed by 5-[N-(3-thia-n-butyl)carbamoyl]thieno[2,3-b]thiophene-2-sulfonamide (1.10 g., 3.27 mmoles) were stirred at room temperature under Argon for 24 hours. The solution was filtered and then stripped of the THF and all but 2-2 mL of water. The product was then crystallized, collected and dried. Recrystallization from nitromethane gave 1.0 g. of 5-[N-(3-oxo-3-thia-n-butyl)-carbamoyl]thieno[2,3-b]thiophene-5-sulfonamide, mp 242°-243° C.

Calc. for $C_{10}H_{12}N_4O_4S_4$: C, 34.08; H, 3.43; N, 7.95. Found: C, 34.36; H, 3.23; N, 8.12.

EXAMPLE VII

5-[N-2-(N'-Morpholino)ethylcarbamoyl]thieno[2,3-b]thiophene-2-sulfonamide hydrochloride

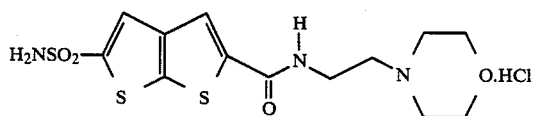

Step A:
5-[N-2-(N'-Morpholino)ethylcarbamoyl]thieno[2,3-b]thiophene-2-sulfonamide A mixture of 5-Methoxycarbonylthieno[2,3-b]thiophene-2-sulfonamide (0.83 g., 3 mmoles), 2-[N-(morpholino)]ethylamine (1.17 g., 9 mmoles) and methanol (4 mL) was refluxed for 72 hours. The methanol was evaporated in vacuo and the residue dissolved in hot THF. The product was adsorbed onto silica gel and the chromatographed product eluted with 10% methanol in chloroform to give 1.37 g of product.

Step B:
5-[N-2-(N'-Morpholino)ethylcarbamoyl]thieno[2,3-b]thiophene-2-sulfonamide hydrochloride 5-[N-2-(N'-Morpholino)ethylcarbamoyl]thieno[2,3-b]thiophene-2-sulfonamide (1.07 g., 2.04 mmole) was dissolved in hot methanol (150 mL) and ethanol (150 mL). This solution was cooled to room temperature, mixed with cold 5.62M HCl in ethanol (0.51 mL, 2.8 mmoles), and allowed to stand for 15 minutes. The mixture was filtered and boiled down to 100 mL. 150 mL of ethanol was added and the solution was boiled down to 100 ml again. This was repeated and allowed to crystallize to give 0.87 g of product, mp 267°-268° C. (D).

EXAMPLE VIII

5-[N-2-(N'-Thiomorpholino)ethylcarbamoyl]-thieno[2,3-b]thiophene-2-sulfonamide hydrochloride

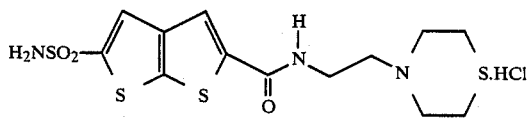

Step A:
5-[N-2-(N'-Thiomorpholino)ethylcarbamoyl]-thieno[2,3-b]thiophene-2-sulfonamide A mixture of 5-Methoxycarbonylthieno[2,3-b]thiophene-2-sulfonamide (0.83 g., 3 mmoles), 2-[N-(thiomorpholino)]ethylamine (1.17 g., 9 mmoles) and methanol (4 mL) was refluxed for 72 hours. The methanol was evaporated in vacuo and the residue dissolved in hot THF. The product was then adsorbed onto silica gel and the product eluted with 10% methanol in chloroform to give 1.37 g of product.

Step B:
5-[N-2-(N'-Thiomorpholino)ethylcarbamoyl]-thieno[2,3-b]thiophene-2-sulfonamide hydrochloride 5-[N-2-(N'-Thiomorpholino)ethylcarbamoyl]-thieno[2,3-b]thiophene-2-sulfonamide (1.07 g., 2.04 mmole) was dissolved in hot methanol (150 mL) and ethanol (150 mL). This solution was cooled to room temperature, mixed with cold 5.62M HCl in ethanol (0.51 mL, 2.8 mmoles), and allowed to stand for 15 minutes. The mixture was filtered and boiled down to 100 mL. 150 mL of ethanol was added and the solution was boiled down to 100 ml again, to give 0.87 g of product, mp 214°-215° C. (D).

EXAMPLE IX

5-{N-[(N',N'-Bis(2-Methoxyethyl)aminoethyl]carbamoyl}thieno[2,3-b]thiophene-2-sulfonamide hydrochloride

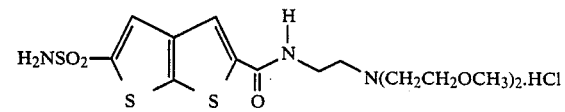

Step A:
5-{N-[(N',N'-Bis(2-Methoxyethyl)aminoethyl]carbamoyl}thieno[2,3-b]thiophene-2-sulfonamide A mixture of 5-Methoxycarbonylthieno[2,3-b]thiophene-2-sulfonamide (0.83 g., 3 mmoles), N,N-Bis(2-Methoxyethyl)aminoethylamine(1.17 g., 9 mmoles) and methanol (4 mL) was refluxed for 72 hours. The methanol was evaporated in vacuo and the residue dissolved in hot THF. The product was then adsorbed onto silica gel, and the chromatographed product eluted with 10% methanol in chloroform to give 1.37 g of product.

Step B:
5-{N-[(N',N'-Bis(2-Methoxyethyl)aminoethyl]carbamoyl}thieno[2,3-b]thiophene-2-sulfonamide hydrochloride 5-{N-[N',N'-Bis(2-Methoxyethyl)aminoethyl]carbamoyl}thieno[2,3-b]thiophene-2-sulfonamide (1.07 g., 2.04 mmole) was dissolved in hot methanol (150 mL) and ethanol (150 mL). This solution was cooled to room temperature, mixed with cold 5.62M HCl in ethanol (0.51 mL, 2.8 mmoles) and allowed to stand for 15 minutes. This solution was then filtered and boiled down to 100 mL. 150 mL of ethanol was added and the resulting solution was boiled down to 100 ml. This step was repeated and crystallization yielded 0.87 g of product, mp 75°-80° C. (D).

Using similar reaction methods to those described in detail above, compounds of formula I having the following substituents are prepared:

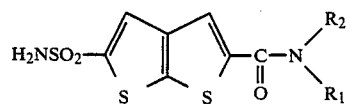
I
| R₁ | R₂ |
|---|---|
| H | 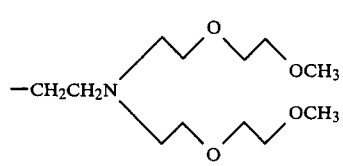 |
| H | 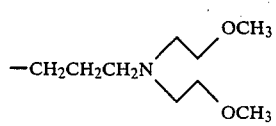 |
| H | 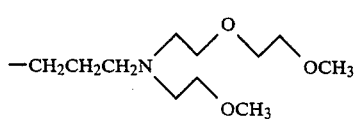 |
| H | 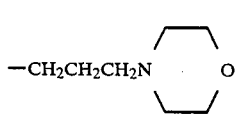 |
| H | 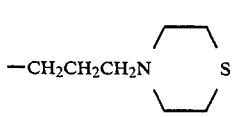 |
| H | 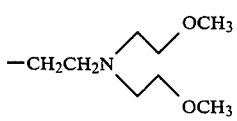 |
| CH₃ | 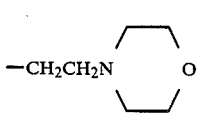 |
| CH₃ | 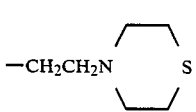 |
| CH₃ | 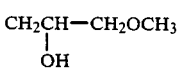 |
| CH₂CH₂OH | 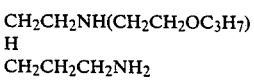 |
| (CH₂)₂O(CH₂)₂OCH₃ | CH₂CH₂NH(CH₂CH₂OC₃H₇) |
| (CH₂)₂O(CH₂)₂NHCH₃ | H |
| (CH₂)₂O(CH₂)₃N(CH₃)(CH₂CH₂OCH₃) | CH₂CH₂CH₂NH₂ |
| (CH₂)₂SO₂CH₃ | 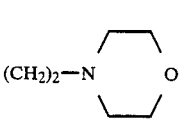 |

-continued

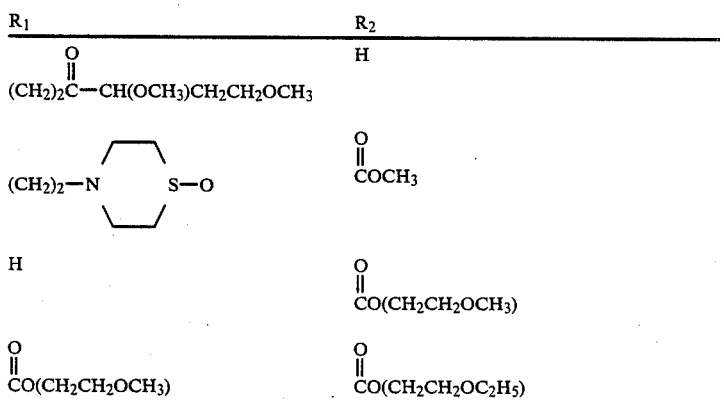

| $R_1$ | $R_2$ |
|---|---|
| $(CH_2)_2\overset{\overset{O}{\|}}{C}-CH(OCH_3)CH_2CH_2OCH_3$ | H |
| $(CH_2)_2-N\diagup\diagdown S-O$ | $\overset{\overset{O}{\|}}{C}OCH_3$ |
| H | $\overset{\overset{O}{\|}}{C}O(CH_2CH_2OCH_3)$ |
| $\overset{\overset{O}{\|}}{C}O(CH_2CH_2OCH_3)$ | $\overset{\overset{O}{\|}}{C}O(CH_2CH_2OC_2H_5)$ |

What is claimed is:

1. A compound of structural formula:

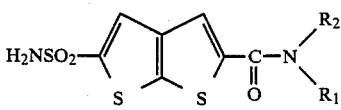

or ophthamologically or pharmaceutically acceptable salt thereof, wherein
$R_1$ and $R_2$ are independently selected from hydrogen or $C_{1-6}$ straight or branched alkyl, either unsubstituted or substituted with:
(a) amino;
(b) di($C_{1-3}$ alkyl)amino;
(c) [$C_{1-3}$ alkoxy-$C_{2-4}$ alkyl]amino;
(d) di[($C_{1-3}$ alkoxy)-$C_{2-4}$ alkyl]amino;
(e) di[$C_{1-3}$ alkoxy-($C_{2-4}$ alkoxy)$_n$($C_{2-6}$ alkyl)]-amino, wherein n=1-4;
(f) $C_{1-4}$ alkoxy;
(g) $C_{1-4}$ alkoxy-($C_{2-4}$ alkoxy)$_n$, wherein n=1-4;
(h) $C_{1-6}$ alkylamino-($C_{2-4}$ alkoxy)$_n$, wherein n=1-4;
(i) hydroxy;
(j) $C_{1-3}$ alkylsulfonyl;
(k) $C_{1-3}$ alkylsulfinyl;
(l) morpholino;
(m) thiomorpholino;
(n) thiomorpholino-S-oxide;

(o) $-\overset{\overset{O}{\|}}{C}-[C_{2-4}\text{ alkyl-}(C_{2-4}\text{ alkoxy})_n]$,
wherein n = 1-4;

(p) $-\overset{\overset{O}{\|}}{C}O-(C_{1-6}\text{ alkyl})$;

(q) $-\overset{\overset{O}{\|}}{C}O-[C_{2-4}\text{ alkyl-}C_{2-4}\text{ alkoxy})_n]$,
wherein n = 1-4;

(r) [($C_{1-3}$ alkoxy)($C_{2-4}$ alkoxy)($C_{1-3}$ alkyl)][($C_{1-3}$ alkoxy)($C_{1-3}$ alkyl) amino;
(s) [($C_{1-3}$ alkoxy)($C_{2-4}$ alkoxy)($C_{1-3}$ alkyl)] amino; or
(t) [($C_{1-3}$ alkoxy)($C_{2-4}$ alkyl)][($C_{1-3}$ alkyl)] amino ($C_{1-3}$ alkoxy);
provided that no more than one heteroatom is bonded to any one carbon.

2. The compound of claim 1, which is:
5-[N-(2,2-Dimethylaminoethyl)carbamoyl]-thieno[2,3-b]thiophene-2-sulfonamide;
5-(N-Methylcarbamoyl)thieno[2,3-b]thiophene-2-sulfonamide;
5-[N-Methoxyethoxypropylcarbamoyl)thieno[2,3-b]thiophene-2-sulfonamide;
5-[N,N-Bis(Hydroxyethylcarbamoyl]thieno[2,3-b]thiophene-2-sulfonamide;
5-[N-(3-Oxo-3-thia-n-butyl)carbamoyl)thieno[2,3-b]thiophene-2-sulfonamide;
5-[N-(2,3-Dihydroxypropyl)carbamoyl]thieno[2,3-b]thiophene-2-sulfonamide;
5-N-2-(N'Morpholino)ethylcarbamoyl]thieno[2,3-b]thiophene-2-sulfonamide;
5-[N-2-(N'-Thiomorpholino)ethylcarbamoyl]-thieno[2,3-b]thiophene-2-sulfonamide;
5-N-[N',N'-Bis(Methoxyethyl)aminoethyl]carbamoyl thieno[2,3-b]thiophene-2-sulfonamide;
and pharmaceutically acceptable salts thereof.

3. An ophthalmic composition for the topical treatment of glaucoma and elevated intraocular pressure, comprising an ophthalmologically acceptable carrier and an effective intraocular pressure lowering amount of a compound with structural formula:

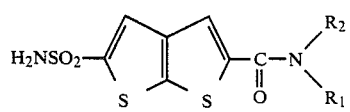

or an opthalmologically acceptable salt thereof, wherein $R_1$ and $R_2$ are as defined in claim 1.

4. The composition of claim 3, wherein the compound is:

5-[N-(2,2-Dimethylaminoethyl)carbamoyl]-
thieno[2,3-b]thiophene-2-sulfonamide;
5-(N-Methylcarbamoyl)thieno[2,3-b]thiophene-2-sulfonamide;
5-(N-Methoxyethoxypropylcarbamoyl)thieno[2,3-b]thiophene-2-sulfonamide;
5-[N-(3-Oxo-3-thia-n-butyl)carbamoyl]thieno[2,3-b]thiophene-2-sulfonamide;
5-[N-(2,3-Dihydroxypropyl)carbamoyl]thieno[2,3-b]thiophene-2-sulfonamide;
5-[N,N-Bis(Hydroxyethyl)carbamoyl]thieno[2,3-b]thiophene-2-sulfonamide;
5-[N-2-(N'-Morpholino)ethylcarbamoyl]thieno[2,3-b]thiophene-2-sulfonamide;
5-[N-2-(N'-Thiomorpholino)ethylcarbamoyl]-
thieno[2,3-b]thiophene-2-sulfonamide;
5-{N-[N',N'-Bis(Methoxyethyl)aminoethyl]carbamoyl}thieno[2,3-b]thiophene-2-sulfonamide;
and pharmaceutically acceptable salts thereof.

5. A method of treating glaucoma and elevated intraocular pressure which comprises topical ocular application to a patient in need of such treatment of an effective intraocular pressure lowering amount of a compound with structural formula

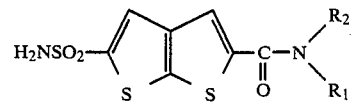

or an ophthalmologically acceptable salt thereof, wherein $R_1$ and $R_2$ are as defined in claim 1.

6. The method of claim 5 wherein the compound is
5-[N-(2,2-Dimethylaminoethyl)carbamoyl]-
thieno[2,3-b]thiophene-2-sulfonamide;
5-(N-Methylcarbamoyl)thieno[2,3-b]thiophene-2-sulfonamide;
5-(N-Methoxyethoxypropylcarbamoyl)thieno[2,3-b]thiophene-2-sulfonamide;
5-[N-(3-Oxo-3-thia-n-butyl)carbamoyl]thieno[2,3-b]thiophene-2-sulfonamide;
5-[N-(2,3-Dihydroxypropyl)carbamoyl]thieno[2,3-b]thiophene-2-sulfonamide;
5-[N,N-Bis(Hydroxyethyl)carbamoyl]thieno[2,3-b]thiophene-2-sulfonamide;
5-[N-2-(N'-Morpholino)ethylcarbamoyl]thieno[2,3-b]thiophene-2-sulfonamide;
5-[N-2-(N'-Thiomorpholino)ethylcarbamoyl]-
thieno[2,3-b]thiophene-2-sulfonamide;
5-{N-[N',N'-Bis(Methoxyethyl)aminoethyl]carbamoyl}thieno[2,3-b]thiophene-2-sulfonamide;
and pharmaceutically acceptable salts thereof.

* * * * *